United States Patent [19]

Ogawa et al.

[11] Patent Number: 4,948,899

[45] Date of Patent: Aug. 14, 1990

[54] 1,4-DIHYDROPYRIDINE DERIVATIVES

[75] Inventors: Toshihisa Ogawa; Tomomi Ota; Shuichi Sato, all of Ageo; Takemi Sunaga, Tokyo; Yoshiaki Watanabe, Kodaira; Katsuo Hatayama, Omiya, all of Japan

[73] Assignee: Taisho Pharmaceutical Co., Ltd., Japan

[21] Appl. No.: 397,850

[22] Filed: Aug. 24, 1989

[30] Foreign Application Priority Data

Sep. 5, 1988 [JP] Japan .................. 63-221963

[51] Int. Cl.$^5$ .......................... C07D 211/86
[52] U.S. Cl. .................................. 546/321
[58] Field of Search ........................ 546/321

[56] References Cited

U.S. PATENT DOCUMENTS 4,537,881  8/1985  Heiker et al. .............. 546/268

Primary Examiner—Jane T. Fan
Attorney, Agent, or Firm—Lorusso & Loud

[57] ABSTRACT

A 1,4-dihydropyridine derivative represented by the formula

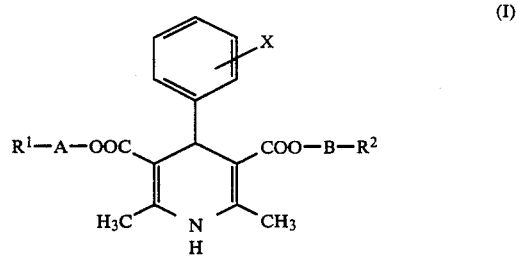

(I)

wherein $R^1$ is a hydrogen atom, an alkoxy group having 1 to 4 carbon atoms, a mercapto group, an alkylcarbonylthio group in which the alkyl group has 1 to 4 carbon atoms or a benzoylthio group, $R^2$ is a mercapto group, an alkylcarbonylthio group in which the alkyl group has 1 to 4 carbon atoms, a benzoylthio group or a 2-cyanoethylthio group, A and B are the same or different and are each an alkylene group having 1 to 4 carbon atoms, and X is a hydrogen atom, a halogen atom, a nitro group or a trifluoromethyl group is disclosed. These compounds increase the therapeutic effect of drug-resistant cancers.

6 Claims, No Drawings

1,4-DIHYDROPYRIDINE DERIVATIVES

BACKGROUND OF THE INVENTION

1. Field of the Invention

The present invention relates to 1,4-dihydropyridine derivatives having the increasing activity of the cytotoxicity of anticancer agents in the drug-resistant cancer.

2. Description of the Prior Art

As 1,4-dihydropyridine derivatives having the increasing activity of the cytotoxicity of anticancer agents in the drug-resistant cancer, there have been known nicardipine and the like in the past [T. Tsuruo et al., Cancer Res., vol. 43, page 2905 (1983)].

The present inventors have found that 1,4dihydropyridine derivatives having the carboxyl groups to which specific groups are introduced enhance the therapeutic effect of anticancer agents with low side-effect, and have accomplished the present invention.

SUMMARY OF THE INVENTION

An object of the present invention is to provide a 1,4-dihydropyridine derivative represented by the formula:

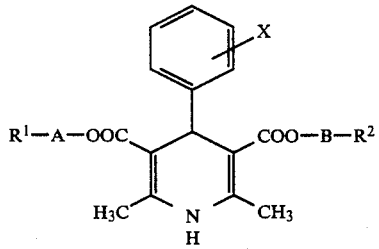

(I)

wherein $R^1$ is a hydrogen atom, an alkoxy group having 1 to 4 carbon atoms, a mercapto group, an alkylcarbonylthio group in which the alkyl group has 1 to 4 carbon atoms or a benzoylthio group, $R^2$ is a mercapto group, an alkylcarbonylthio group in which the alkyl group has 1 to 4 carbon atoms; a benzoylthio group or a 2-cyanoethylthio group, A and B are the same or different and are each an alkylene group having 1 to 4 carbon atoms, and X is a hydrogen atom, a halogen atom, a nitro group or a trifluoromethyl group.

DETAILED DESCRIPTION OF THE INVENTION

In the present invention, the alkylene group having 1 to 4 carbon atoms for A and B refers to a straight or branched chain alkylene group such as, for example, a methylene group, an ethylene group, a trimethylene group, a 1-methylethylene group, a 2-methylethylene group and a tetramethylene group.

The alkoxy group having 1 to 4 carbon atoms for $R^1$ refers to a straight or branched chain alkoxy group such as, for example, a methoxy group, an ethoxy group, a propoxy group and an isopropoxy group.

The alkylcarbonylthio group in which the alkyl group has 1 to 4 carbon atoms for $R^1$ and $R^2$ refers to a straight or branched chain alkylcarbonylthio group such as, for example, an acetylthio group, a propionylthio group and a butyrylthio group.

The halogen atom for X refers to a fluorine, chlorine, bromine and iodine atom.

Preferred compounds of the present invention are 2,6-dimethyl-4-(3-nitrophenyl)-1,4-dihydropyridine-3,5dicarboxylic acid 3-ethyl ester 5-(2-acetylthioethyl) ester, 2,6-dimethyl-4-(3-nitrophenyl)-1,4-dihydropyridine- -; 3,5-dicarboxylic acid 3-methoxyethyl ester 5-[3-(2-cyanoethylthio)propyl]ester, 2,6-dimethyl-4-(3-nitrophenyl)1,4-dihydropyridine-3,5-dicarboxylic acid 3-methoxyethyl ester 5-(2-acetylthioethyl) ester, 2,6-dimethyl-4-(3-nitrophenyl)-1,4-dihydropyridine-3,5-dicarboxyli acid 3-methyl ester 5-(2-acetylthioethyl) ester and 2,6-dimethyl-4(3-nitrophenyl)-1,4-dihydropyridine-3,5-dicarboxylic acid bis(3-acetylthiopropyl) ester.

The 1,4-dihydropyridine derivatives of the present invention can be prepared, for example, according to the following Processes (1) to (5) wherein the compounds having 1,4-dihydropyridine skeleton can be prepared according to the methods described in J. Org. Chem., vol. 16, page 1259 (1951) or Ber., vol. 31, page 743 (1898).

Process (1): A benzaldehyde derivative represented by the formula;

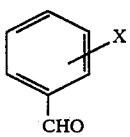

(II)

(wherein X is as defined above), an acetoacetate represented by the formula:

(III)

(wherein B and $R^2$ are defined above) and 3-aminocrotonate represented by the formula:

(IV)

(wherein A and $R^1$ are as defined above) are heated together in an organic solvent for reaction to give a compound of the present invention. In this reaction, a secondary amine, or an inorganic or organic acid salt thereof may be added. Examples of the secondary amine are dimethylamine, diethylamine, diisopropylamine, pyrrolidine, piperidine, piperazine, N-methylpiperazine and morpholine. Examples of the inorganic acid salt are salts with hydrochloric acid, sulfonic acid, nitric acid, hydrobromic acid and phosphoric acid, and examples of the organic acid salt are salts with formic acid, acetic acid, trifluoroacetic acid, propionic acid, benzoic acid and 1 p-toluenesulfonic acid.

The organic solvents used in the reaction may be methanol, ethanol, 2-propanol, dioxane, tetrahydrofuran, benzene and toluene.

The reaction temperature is preferably the boiling point of the solvent, and more preferably 70 to 100° C.

Process (2): The compound of Formula II is reacted with a compound of Formula III in the presence of a secondary amine or an inorganic or organic acid salt thereof in an organic solvent at 0 to 150° C. to give a benzylidene derivative represented by the formula:

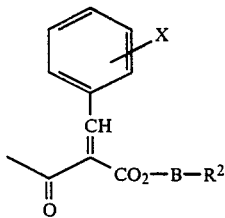

(wherein X, B and $R^2$ are as defined above), which is then reacted with a compound of Formula IV in an organic solvent or without solvent with heating at 50 to 100° C. to give the compound of the present invention.

The secondary amine and the inorganic or organic salt thereof are the same as those exemplified in Process (1).

Examples of the organic solvent are benzene, toluene, xylene, ethanol, 2-propanol, dioxane and tetrahydrofuran.

Process (3): A compound represented by the formula:

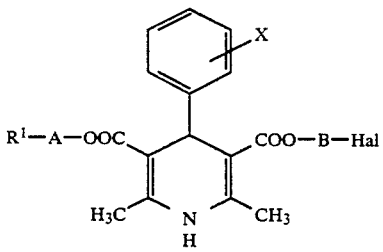

(wherein Hal is a halogen atom, X, A, B and $R^1$ are as defined above), obtained according to a process similar to Process (1) or (2), is reacted with a compound of $R^2$ (wherein $R^2$ is as defined above) in an organic solvent in the presence of a basic catalyst or a quarternary ammonium salt at 0 to 50° C. to give a compound of the present invention.

Examples of the organic solvent used are methanol, ethanol, dichloroethane, N,N-dimethylformamide, benzene: toluene and tetrahydrofuran.

Examples of the inorganic catalyst are alkalis such as sodium hydroxide, potassium hydroxide and potassium carbonate, and examples of the quarternary ammonium salt are triethylbenzyl ammonium chloride and the like.

Process (4): The compound of Formula I wherein the substituents -A-$R^1$ and -B-$R^2$ are the same group can be prepared by the following method: namely, a compound represented by the formula:

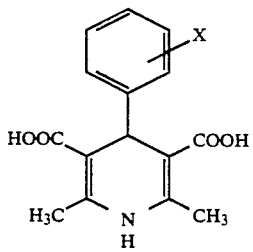

(V)

(wherein X is as defined above) is reacted with a carboxylic acid activator in an inert solvent in the presence of a catalyst or without catalyst at 40° C. or below to give an activating ester of a 1,4-dihydropyridine-3,5-dicarboxylic acid represented by the formula:

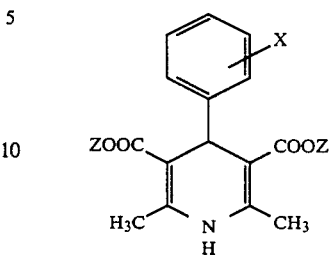

(wherein X is as defined above, and Z is an activating residue of a carboxylic acid), which is then reacted with an alcohol represented by HO—B—$R^2$ (wherein B and $R^2$ are as defined above) to give the compound of the present invention.

The carboxylic acid activator used herein refers to those which rise the activation of the carboxyl groups of the compound of Formula V in the reaction such as, for example, acetic anhydride, trifluoroacetic anhydride, N-ethoxycarbonyl-2-ethoxy-1,2-dihydroquinoline, 2-chloro1-methylpyridinium chloride, 2,2″-dipyridyl disulfide, 3-nitro-2-pyridinesulfinylchloride, triphenylphosphinediethyl azodicarboxylate, 1,1′-carbonyldiimidazole and dimethyl(chloromethylidene)ammonium chloride.

Examples of the inert solvent are halogenated hydrocarbons such as dichloromethane and chloroform, ethers such as tetrahydrofuran, 1,2-dimethoxyethane and dioxane, and hydrocarbons such as benzene and toluene.

Examples of the catalyst are organic acid halides such as acetyl chloride and benzoyl chloride, inorganic bases such as sodium hydroxide, potassium hydroxide, sodium carbonate, potassium carbonate, sodium hydrogen carbonate and sodium hydride, organic bases such as triethylamine and pyridine, and molecular seives.

Process (5): The compounds of Formula I wherein $R^2$ is a cyanoethylthio group can be also prepared by the following process: A compound represented by the formula:

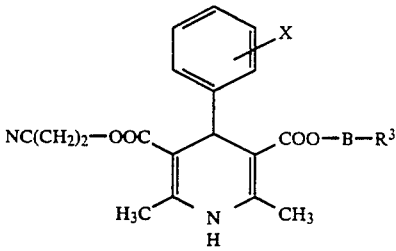

(wherein $R^3$ is an alkylcarbonylthio group in which the alkyl group has 1 to 4 carbon atoms or a benzoylthio group, and B and X are as defined above), which can be prepared by a procedure similar to that of Process (1) or (2), is reacted in a mixture of water and an organic solvent in the presence of a base at 0 to 50° C. to give a compound of the formula:

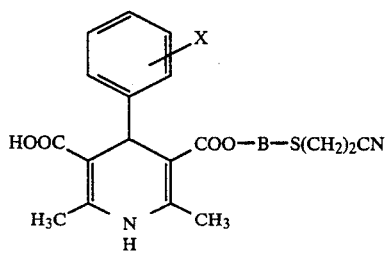

(wherein B and, X are as defined above).

Examples of the organic solvent are methanol, ethanol, acetone and dioxane, and examples of the base are alkalis such as sodium hydroxide and potassium hydroxide.

Then, the compound of Formula VI is reacted with an alcohol of the formula HO—A—$R^1$ (wherein A and $R^1$ are as defined above) according to Process (4) to give the compound of the present invention.

The compounds of the present invention have the increasing effect on the sensitivity of the anticancer agent in the cancer cells, and therefore increase the therapeutic effect of the anticancer agent-resistant cancers. For the purpose, these compounds can be administered orally or parenterally in a conventional dosage forms such as tablets, powders, granules, capsules, solutions and injectional solutions, each of which can be prepared in accordance with ordinary pharmaceutical practices.

When the compound of the present invention is used with the other anticancer agent, the dose depends on the age, body weight, response of the patients, route of the administration or time of the administration, but usually it may be from 0.1 to 100 mg/day.

EXPERIMENT 1

[Uptake effect of the anticancer agent into drug-resistant cancer cells]

In RPMI-1640 culture solution containing 5% bovine fatal serum was suspended adriamycin-resistant strain 2780 AD of human ovarian cancer cells [A. M. Rogan et al., Science, 224, 994 –996 (1984)]in the amount of 1 x 106/ml. The cancer cell suspension was seeded in the amount of 1 ml per well of a 16 cm diameter 24-multiwell culture plate and cultured at 37° C under 5% $CO_2$ After 24 hours, the culture solution was replaced with 0.5 ml of RPMI-1640 culture solution containing 20 nmol of 3H-vincristine (1×$10^4$dpm/pmol), 5% bovine fatal serum and 10 mmol of HEPES buffer. A solution of the test compound in dimethyl sulfoxide was diluted with phosphate-buffer, and 5 μlof the solution was added to the above culture solution (the concentrations of the test compound were 0.1 μg/ml and 10 μg/ml in the reaction solution). Cultivation was continued under 5% $CO_2$ at 37° C. for 2 hours, and the cells were washed with cooled phosphate-buffer saline. To this was added 0.5 ml of 0.2 N sodium hydroxide, and the mixture was placed in a vial and warmed at 56° C. for 30 to 60 minutes on a water bath to dissolve the cells. Four ml of acidified Aquasol 2 was added, and the uptake amount of $^3$H-vincristine into the cells was determined by means of the liquid scintillation counter. These determination values are expressed as compared with 1.0 of the value of the drug untreated group.

TABLE 1

| Test compound | Uptake of the anticancer agent | |
|---|---|---|
| | 1 μg/ml | 10 μg/ml |
| Compound 1 | 1.7 | 21 |
| Compound 2 | 1.3 | 27 |
| Compound 3 | 1.5 | 33 |
| Compound 4 | 2.0 | 23 |
| Compound 5 | 2.5 | 12 |

Note: Compounds 1 to 5 are as defined in the following Examples.

The present invention is illustrated by the following examples in more detail. Example 1
2,6-Dimethyl-4-(3-nitrophenyl)-1,4-dihydropyridine-3,5-dicarboxylic acid 3-methoxyethyl ester -(2-acetylthioethyl) ester (Compound 1)

A solution of 2.04 g of 2-acetylthioethyl acetoacetate, 1.51 g of 3-nitrobenzaldehyde, 1.49 g of methoxyethyl 3-aminocrotonate and 0.15 g of piperidinium acetate in 20 ml of 2-propanol was refluxed for 4 hours. After evaporation of the solvent under reduced pressure, the residue was purified by silica gel column chromatography [eluent: ethyl acetate - hexane (1 : 3)]to give 1.54 g of the title compound. m.p. 136–138° C.

$^1$H-NMR($CDCl_3$) δppm
2.33(3H, s), 2.36(3H, s), 2.38(3H, s),
3.08(2H, t, J=6Hz), 3.37(3H, s),
3.57(2H, t, J=6Hz), 4.1–4.3(4H, m),
5.08(1H, s), 5.75(1H, bs),
7.38(1H, t, J=8Hz), 7.68(1H, d, J=8Hz),
8.02(1H, d, J=8Hz), 8.13(1H, s)

Following a procedure similar to that of Example 1, there were obtained the following compounds.

2,6-Dimethyl-4-(3-nitrophenyl)-1,4-dihydropyroidine-3,5-dicarboxylic acid 3-isopropyl ester -(2-acetylthioethyl) ester
m.p. 82–84° C.
$^1$H-NMR($CDCl_3$) δppm
1.12(3H, d, J=6Hz), 1.27(3H, d, J=6Hz),
2.33(3H, s), 2.36(3H, s), 2.38(3H, s),
3.08(2H, t, J=7Hz), 4.15(2H, t, J=7Hz),
4.96(2H, septet, J=6Hz), 5.06(1H, s),
5.73(1H, bs), 7.39(1H, t, J=8Hz),
7.65(1H, d, J=8Hz), 8.01(1H, d, J=8Hz),
8.15(1H, s)

2,6-Dimethyl-4-(3-nitrophenyl)-1,4-dihydropyridine-3,5-dicarboxylic acid 3-methyl ester 5-(2ester (Compound 2)
m.p. 104–106° C.
$^1$H-NMR($CDCl_3$) δppm
2.33(3H, s), 2.38(6H, s),
3.09(2H, t, J=6Hz), 3.66(3H, s),
4 15(2H, dt, J2Hz, 6Hz), 5.06(1H, s),
5.77(1H, bs), 7.38(1H, t, J=8Hz),
7.65(1H, d, J=8Hz), 8.00(1H, d, J=8Hz),
8.13(1H, s)

2,6-Dimethyl-4-(3-chlorophenyl)-1,4-dihydropyridine-3,5-dicarboxylic acid 3-methyl ester 5-(2ester
m.p. 95–97° C.
$^1$H-NMR($CDCl_3$) δppm
2.33(9H, s), 3.00(2H, t, J=6Hz),
3.66(3H, s), 4.1–4.3(2H, m), 4.95(1H, s), 1 25 H, bs),
7.1–7.3(4H, m) ". 5.73(1

2.6-Dimethyl-4-phenyl-1,4-dihydropyridine-3,5dicarboxy ic acid 3-methyl ester 5-(2-acetylthioethyl) ester
$^1$H-NMR($CDCl_3$) δppm
2.32(9H, s), 3.08(2H, t, J=6Hz),
3.64(3H, s), 4.15(2H, dt, J=2Hz, 6Hz), 4.96(1H, s), 5.83(1H, bs), 7.1–7.3(5H, m)

2,6-Dimethyl-4-(3-trifluoromethylphenyl)-1,4-dihydropyridine-3,5-dicarboxylic acid 3-methyl ester 5-(2-acetylthioethyl) ester m. p. 75–77° C.

$^1$H-NMR(CDCl$_3$) δppm 2.32(3H, s), 2.35(3H, s), 2.36(3H, s), 3.08(2H, t, J=6Hz(, 3.65(3H, s), 4.15(2H, dt, J=2Hz, 6Hz), 5.01(1H, s), 5.70(1H, bs), 7.3–7.6(4H, m)

EXAMPLE 2

2,6-Dimethyl-4-(3-nitrophenyl)-1,4-dihydropyridine-3,5-dicarboxylic acid 3-ethyl ester 5-(2-acetylthioethyl) ester (Compound 3)

A solution of 7.0 g of 2-acetylthioethyl acetoacetate, 5.14 g of 3-nitrobenzaldehyde and 0.99 g of piperidinium acetate in 100 ml of benzene was heated at reflux under azeotropic dehydration conditions for 2 hours. The reaction mixture was poured into water and extracted with benzene, and the extract was washed with water and dried over anhydrous sodium sulfate. Evaporation of the solvent under reduced pressure gave 9.83 g of 2-acetylthioethyl 2-(3-nitrobenzilidene)acetoacetate.

Then 8.0 g of this compound was mixed with a solution of 2.71 g of ethyl 3-aminocrotonate in 80 ml of 2-propanol, and the mixture was refluxed for 3 hours. After evaporation of the solvent under reduced pressure, the residue was applied to silica gel column chromatography [eluent: ethyl acetate - hexane (1:1)] and then recrystalized from dichloromethane - 2-propanol to give 5.65 g of the title compound as yellow crystals.

m.p. 98–101° C.

$^1$HMR(CDCl$_3$) δppm 1.25(3H, t, J=32Hz), 2.32(3H, s), 2.36(3H, s), 2.38(3H, s), 3.09(2H, t, J=6Hz), 4.13(2H, m), 4.14(2H, q, J=6Hz), 5.08(1H, s), 5.80(1H, s), 7.3–8.2(4H, m), 7.65(1H, d, J=8Hz), 8.00(1H, d, J=8Hz), 8.13(1H, s)

Following the process similar to that of Example 2, there were synthesized the following compounds.

2,6-Dimethyl-4-(3-nitrophenyl)-1,4-dihydropyridine-3,5-dicarboxylic acid 3-isopropyl ester 5-(3-acetylthiopropyl) ester m.p. 92–93° C.

$^1$H-NMR(CDCl$_3$) δppm 1.12(3H, d, J=6Hz), 1.27(3H, d, J=6Hz), 1.86(1H, m), 2.32(3H, s), 2.35(3H, s), 2.38(3H, s), 2.78(2H, t, J=6Hz), 4.0–4.2(2H, m), 4.97(1H, m), 5.08(1H, s), 5.95(1H, bs), 7.41(1H, t, J=8Hz), 7.66(1H, d, J=8Hz), 8.00(1H, d, J=8Hz), 8.13(1H, s)

2,6-Dimethyl-4-(3-nitrophenyl)-1,4-dihydropyridine-3,5-dicarboxylic acid 3-ethyl ester 5-(3-acetylthiopropyl) ester m.p. 73–75° C.

$^1$H-NMR(CDCl$_3$) δppm 1.24(3H, t, J=7Hz), 1.86(2H, m), 2.33(3H, s), 2.36(3H, s), 2.78(2H, t, J=7Hz), 4.0–4.2(4H, m), 5.10(1H,s), 5.80(1H, bs), 7.38(1H, t, J=8Hz), 7.65(1H, d, J=8Hz), 8.01(1H, d, J=8Hz), 8.13(1H, s)

2,6-Dimethyl-4-(3-nitrophenyl)-1,4-dihydropyridine-3,5-dicarboxylic acid 3-methoxyethyl ester 5-(3-acetylthiopropyl) ester m.p. 104–105° C.

$^1$H-NMR(CDCl$_3$) δppm 1.86(2H, m), 2.32(3H, s), 2.36(3H, s), 2.38(3H, s), 2.79(2H, t, J=6Hz), 3.36(3H, s), 3.57(2H, t, J=4Hz), 4.0–4.3(4H, m), 5.11(1H,s), 6.00(1H, bs), 7.38(1H, t, J=8Hz), 7.68(1H, d, J=8Hz), 8.00(1H, d, J=8Hz), 8.12(1H, s)

2,6-Dimethyl-4-(3-nitrophenyl)-1,4-dihydropyridine-3,5-dicarboxylic acid 3-methyl ester 5-(3-benzoylthiopropyl) ester m.p. 112–114° C.

$^1$H-NMR(CDCl$_3$) δppm 1.98(2H, m), 2.37(3H, s), 2.40(3H, s), 2.99(2H, t, J=6Hz), 3.67(3H, s), 4.0–4.3(2H, m), 5.13(1H, s), 5.83(1H, bs), 7.3–7.7(5H, m), 7.9–8.2(4H, m)

2,6-Dimethyl-4-(3-nitrophenyl)-1,4-dihydropyridine-3,5-dicarboxylic acid 3-methoxyethyl ester 5-(3-benzoylthiopropyl) ester m.p. 87–88° C.

$^1$H-NMR(CDCl$_3$) δppm 1.97(2H, m), 2.34(3H, s), 2.38(3H, s), 3.00(2H, t, J=6Hz), 3.34(3H, s), 3.57(2H, t, J=4Hz), 4.0–4.3(4H, m), 5.15(1H, s), 6.28(1H, bs), 7.3–7.6(4H, m), 7.73(1H, d, J=8Hz), 7.9–8.0(3H, m), 8.16(1H, s)

EXAMPLE 3

2,6-Dimethyl-4-(3-nitrophenyl)-1,4-dihydropyridine-3,5-dicarboxylic acid 3-methyl ester 5-(3-acetylthiopropyl) ester To a solution of 0.30 g of thioacetic acid in 20 ml of N,N-dimethylformamide cooled on ice was added 0.50 g of potassium carbonate, and the mixture was stirred for 10 minutes. Then, 0.90 g of 2,6-dimethyl-4-(3-nitrophenyl)-1,4-dihydropyridine-3,5-dicarboxylic acid 3-methyl ester 5-(3-bromopropyl) ester was added, and the mixture was stirred at room temperature for 24 hours. The reaction solution was poured into water and extracted with dichloromethane. The organic layer was washed with water and brine successively,m and dried over magnesium sulfate.

After evaporation of the solvent under reduced pressure, the residue was purified by silica gel column chromatography [eluent : ethyl acetate - hexane (1:4)] to give 0.82 g of the title compound.

m.p. 117–119° C.

$^1$H-NMR(CDCl$_3$) δppm 1.88(2H, m), 2.33(3H, s), 2.36(3H, s), 2.39(3H, s), 2.88(2H, t, J=6Hz), 3.67(3H, s), 4.0–4.2(2H, m), 5.11(1H, s), 6.05(1H, bs), 7.38(1H, t, J=8Hz), 7.66(1H, d, J=8Hz), 8.01(1H, d, J=8Hz), 8.12(1H,s)

Following a procedure similar to that of Example 3, there were synthesized the following compounds.

2,6-Dimethyl-4-(3-nitrophenyl)-1,4-dihydropyridine-3,5-dicarboxylic acid 3-methyl ester 5-(2-benzoylthioethyl) ester m.p. 112–114° C.

$^1$H-NMR(CDCl$_3$) δppm 2.37(3H, s), 2.39(3H,s),
3.30(2H, t, J=7Hz), 3.64(3H, s),
4.27(2H, dt, J=4Hz), 5.01(1H,s),
5.86(1H, bs), 7.35(1H, t, J=8Hz),
7.46(2H, t, J=7Hz), 7.60(1H, t, J=7Hz),
7.66(1H, d, J=8Hz), 7.92(2H, d, J=7Hz),
7.98(1H, d, J=8Hz), 8.12(1H, s)

2,6-Dimethyl-4-(3-nitrophenyl)-1,4-dihydropyridine-3,5-dicarboxylic acid 3-methyl ester 5-(3-mercaptopropyl) ester $^1$H-NMR(CDCl$_3$) δppm
1.97(2H, quintet, J=7Hz), 2.37(3H,s),
2.39(3H, s), 2.53(2H, dt, J=2Hz),
2.6–2.8(1H, m), 3.66(3H, s),
4.0–4.3(2H, m), 5.08(1H, s),
5.83(1H, bs), 7.38(1H, t, J=8Hz),
7.63(1H, d, J=8Hz), 8.00(1H, d, J=8Hz),
8.10(1H, s)

EXAMPLE 4

2,6-Dimethyl-4-(3-nitrophenyl)-1,4-dihydropyridine-3,5-dicarboxylic acid bis(2-acetylthioethyl) ester A solution of 1.27 g of 2,6-dimethyl -4-(3-nitrophenyl)-1,4-dihydropyridine-3,5-dicarboxylic acid and 3.06 g of acetic anhydride in 40 ml of dichloromethane was stirred at room temperature for 15 hours, followed by adding 1.15 g of 2-acetylthioethanol and a few drops of acetyl chloride, and then the mixture was stirred at room temperature for 72 hours. The reaction solution was neutralized by adding an aqueous sodium carbonate solution and extracted with chloroform. The organic layer was washed with brine and dried over magnesium sulfate.

After evaporation of the solvent under reduced pressure, the residue was purified by silica gel column chromatography [eluent : ethyl acetate - hexane (1:3)] to give 0.62 g of the title compound.

$^1$H-NMR(CDCl$_3$) δppm
2.05(6H, s), 2.40(6H, s),
3.17(4H, t, J=7Hz), 4.17(4H, t, J=7Hz),
5.47(1H, s), 6.23(1H, bs),
7.42(1H, t, J=8Hz), 7.73(1H, d, J=8Hz),
8.06(1H, d, J=8Hz), 8.15(1H, s)

Following a procedure similar to that of Example 4, there were synthesized the following compounds.

2,6-Dimethyl-4-(3-nitrophenyl)-1,4-dihydropyridine-3,5-dicarboxylic acid bis(2-benzoylthioethyl) ester
m.p. 120–123° C.

$^1$H-NMR(CDCl$_3$) δppm
2.37(6H, s), 3.30(4H, t, J=7Hz),
4.26(4H, dt, J=4Hz, 7Hz), 5.10(1H, s),
6.06(1H, bs), 7.33(1H, t, J=8Hz),
7.44(4H, t, J=7Hz), 7.57(2H, t, J=7Hz),
7.70(1H, d, J=8Hz), 7.93(4H, d, J=7Hz),
7.96(1H, d, J=8Hz), 8.15(1H, s)

2,6-Dimethyl-4-(3-nitrophenyl)-1,4-dihydropyridine-3,5-dicarboxylic acid bis(3-acetylthiopropyl) ester (Compound 4)
m.p. 93–95° C.

$^1$H-NMR(CDCl$_3$) δppm
1.88(4H, quintet, J=7Hz), 2.33(6H, s),
2.38(6H, s), 2.81(4H, dt, J=2Hz, 7Hz),
4.09(4H, dt, J=3Hz, 7Hz), 5.11(1H, s),
5.84(1H, bs), 7.39(1H, t, J=8Hz),
7.67(1H, d, J=8Hz), 8.01(1H, d, J=8Hz),
8.12(1H, s)

2,6-Dimethyl-4-(3-nitrophenyl)-1,4-dihydropyridine-3,5-dicarboxylic acid bis(3-benzoylthiopropyl) ester
m.p. 101–105° C.

$^1$H-NMR(CDCl$_3$) δppm
2.00(4H, quintet, J=7Hz), 2.40(6H, s),
3.02(4H, dt, J=2Hz, 7Hz),
4.17(4H, dt, J=3Hz, 7Hz), 5.17(1H,s),
5.99(1H, bs), 7.37(1H, t, J=8Hz),
7.43(4H, t, J=7Hz), 7.57(2H, t, J=7Hz),
7.74(1H, d, J=8Hz), 7.93(4H, d, J=7Hz),
8.00(1H, d, J=8Hz), 8.17(1H, s)

EXAMPLE 5

2,6-Dimethyl-4-(3-nitrophenyl)-1,4-dihydropyridine-3,5-dicarboxylic acid 3-methoxyethyl ester 5-[3-(2-cyanoethylthio)propyl] ester (compound 5)

A solution of 21.83 g of 3-acetylthiopropyl acetoacetate, 15.11 g of 3-nitrobenzaldehyde, 15.42 g of 2-cyanoethyl 3-aminocrotonate and 2.90 g of piperidinium acetate in 200 ml of 2- propanol was refluxed for 5 hours. The reaction solution was poured into water, extracted with dichloromethane and dried. After evaporation of the solvent under reduced pressure, the residue was dissolved in a mixture of 200 ml of acetone and 100 ml of water, 6.0 g of sodium hydroxide was added, and then the mixture was stirred at room temperature for 2 hours.

The reaction solution was diluted with water and extracted with dichloromethane. In an aqueous layer was dissolved 14.1 g of sodium dihydrogen phosphate, and then phosphoric acid was added until the insolubles precipitated no longer.

Filtration of the precipitate gave 28.0 g of 2,6-dimethyl-4-(3-nitrophenyl)-1,4-dihydropyridine-3,5-dicarboxylic acid 5-[3(2-cyanoethylthio)propyl] ester.

To a solution of 2.17 g of this compound and 1.53 g of acetic anhydride in 50 ml of dichloromethane were added 0.46 g of 2-methoxyethanol and a few drops of acetyl chloride, and the mixture was stirred at room temperature for 2 hours. The reaction solution was poured into an aqueous sodium carbonate solution and separated. The organic layer was dried, and the solvent was evaporated to give the crude crystals, which were then washed with isopropyl ether to give 1.75 g of the title compound.
m.p. 92–94° C.

$^1$H-NMR(CDCl$_3$) δppm
1.88(2H, m), 2.36(3H,x), 2.39(3H, s),
2.52(2H, t, J=7Hz), 2.62(2H, m),
2.75(2H, m), 3.37(3H, s),
3.57(2H, t, J=5Hz), 4.16(2H, m),
4.18(2H, m), 5.10(1H, s), 6.06(1H, s),
7.4–8.2(4H, m)

Following a procedure similar to that of Example 5, there were synthesized the following compounds.

2,6-Dimethyl-4-phenyl-1,4-dihydropyridine-3,5-dicarboxylic acid 3-methyl ester 5-[2-(2-cyanoethylthio)-ethyl] ester
m. p. 112–114° C.

$^1$H-NMR(CDCl$_3$) δppm
2.33(3H, s), 2.36(3H, s),
2.58(2H, t, J=7Hz), 2.7–2.8(4H, m),
3.67(3H, s), 4.1–4.3(2H, m), 4.98(1H, s),
5.71(1H, bs), 7.1–7.3)5H, m)

2,6-Dimethyl-4-(3-trifluoromethylphenyl)-1,4-dihydropyridine-3,5-dicarboxylic acid 3-methyl ester 5-]2-(2-cyanoethylthio)ethyl] ester
m. p. 91–93° C.

$^1$H-NMR(CDCl$_3$) δppm
2.36(3H, s), 2.38(3H, s), 2.60(2H, t, J=8Hz), 2.7–2.9(4H, m),
3.65(3H, s), 4.1–4.3(2H, m), 5.03(1H, s),
5.71(1H, bs), 7.3–7.5(4H, m)

2,6-Dimethyl-4-(3-chlorophenyl)-1,4-dihydropyridine-3,5-dicarboxylic acid 3-methyl ester 5-]2-(2-cyanoethylthio)ethyl] ester m.p. 88–90° C.
$^1$H-NMR(CDCl$_3$) δppm
2.35(3H, s), 2.37(3H, s),
2.61(2H, t, J=6Hz), 2.66(4H, t, J=6Hz),
3.27(3H, s), 4.0–4.4(2H, m), 4.97(1H, s),
5.73(1H, bs), 7.0–7.5(4H, m)

2,6-Dimethyl-4-(3-nitrophenyl)-1,4-dihydropyridine-3,5-dicarboxylic acid 3-methyl ester 5-]2-(2-cyanoethylthio)ethyl] ester m.p. 92–94° C.
$^1$H-NMR(CDCl$_3$) δppm
2.37(3H, s), 2.38(3H, s),
2.64(2H, t, J=6Hz), 2.80(4H, t, J=6Hz),
3.66(3H, s), 4.0–4.4(2H, m),
5.09(1H, s), 5.88(1H, bs),
7.38(1H, t, J=8Hz), 7.65(1H, d, J=8Hz),
8.01(1H, d, J=8Hz), 8.12(1H, s)

2,6-Dimethyl-4-(3-nitrophenyl)-1,4-dihydropyridine-3,5-dicarboxylic acid 3-ethyl ester 5-]2-(2-cyanoethylthio)ethyl] ester $^1$H-NMR(CDCl$_3$) δppm
1.23(3H, t, J=6Hz), 2.37(3H, s),
2.38(3H, s), 2.65(2H, t, J=6Hz),
2.79(4H, t, J=6Hz), 3.9–4.4(4H, m),
5.10(1H, s), 6.00(1H, bs),
7.40(1H, t, J=8Hz), 7.66(1H, d, J=8Hz),
8.01(1H, d, J=8Hz), 8.14(1H, s)

2,6-Dimethyl-4-(3-nitrophenyl)-1,4-dihydropyridine-3,5-dicarboxylic acid 3-isopropyl ester 5-]2-(2-cyanoethylthio)ethyl] ester $^1$H-NMR(CDCl$_3$) δppm
1.11(3H, d, J=6Hz), 1.27(3H, d, J=6Hz),,
2.36(3H, s), 2.38(3H, s),
2.65(2H, t, J=6Hz), 2.79(4H, t, J=6Hz),
4.0–4.4(2H, m), 4.95(1H, septet, J=6Hz),
5.08(1H, s), 6.08(1H, bs),
7.39(1H, t, J=8Hz), 7.66(1H, d, J=8Hz),
8.02(1H, d, J=8Hz), 8.14(1H, s)

2,6-Dimethyl-4-(3-nitrophenyl)-1,4-dihydropyridine-3,5-dicarboxylic acid 3-(2-acetylthioethyl) ester 5-]2(2-cyanoethylthio)ethyl] ester $^1$H-NMR(CDCl$_3$) δppm
2.03(3H, s), 2.36(3H, s), 2.42(3H, s),
2.67(2H, t, J=6Hz), 2.84(2H, t, J=6.5Hz),
2.88(2H, t, J=6.5Hz),
3.09, 3.12(2H, each t, J=6.5Hz),
4.11(2H, t, J=6.5Hz),
4.29, 4.31(2H, each t, J=6.5Hz),
5.29(1H, s), 6.15(1H, s),
7.42(1H, t, J=8Hz), 7.68(2H, dt, J=2Hz, 8Hz),
8.03(1H, dt, J=2Hz, 8Hz), 8.16(1H, t, J=2Hz)

2,6-Dimethyl-4-(3-nitrophenyl)-1,4-dihydropyridine-3,5-dicarboxylic acid 3-(2-acetylthioethyl) ester 5-[3-(2-cyanoethylthio)propyl] ester $^1$H-NMR(CDCl$_3$) δppm
1.99(2H, quintet, J=6.5Hz), 2.03(3H, s),
2.37(3H, s), 2.42(3H, s),
2.63(4H, t, J=6.5Hz), 2.78(2H, t, J=6.5Hz),
3.10, 3.12(2H, each t, J=6.5Hz),
4.12(2H, t, J=6.5Hz),
4.23, 4.24(2H, each t, J=6.5Hz),
5.31(1H, s), 6.00(1H, s),
7.42(1H, t, J=8Hz),
7.66(1H, dt, J=2Hz, 8Hz),
8.04(1H, dt, J=2Hz, 8Hz), 8.13(1H, t, J=2Hz)

2,6-Dimethyl-4-(3-nitrophenyl)-1,4-dihydropyridine-3,5-dicarboxylic acid 3-(2-benzoylthioethyl) ester 5-[3-(2-cyanoethylthio)propyl]ester $^1$H-NMR(CDCl$_3$) δppm
1.88(2H, quintet, J=6.5Hz), 2.38(6H, s),
2.52(2H, t, J=6.5Hz), 2.59(2H, t, J=6.5Hz),
2.72(2H, t, J=6.5Hz), 3.31(2H, t, J=6.5Hz),
4.14(2H, m), 4.27, 4.28(2H, each t, J=6.5Hz),
5.08(1H, s), 5.91(1H, s),
7.38(1H, t, J=8Hz), 7.47(2H, t, J=7.5Hz),
7.60(1H, t, J=7.5Hz),
7.65(1H, dt, J=2Hz, 8Hz),
7.93(2H, d, J=7.5Hz),
7.99(1H, dt, J=2Hz, 8Hz), 8.12(1H, t, J=2Hz)

2,6-Dimethyl-4-(3-nitrophenyl)-1,4-dihydropyridine-3,5-dicarboxylic acid 3-(3-acetylthiopropyl) ester 5-[3-(2-cyanoethylthio)propyl]ester $^1$H-NMR(CDCl$_3$) δppm
1.87(2H, quintet, J=7Hz),
1.91(2H, quintet, J=7Hz), 2.33(3H, s),
2.37(6H, s), 2.53(2H, t, J=7Hz),
2.62(2H, t, J=6.5Hz), 2.76(2H, t, J=6.5Hz),
2.82(2H, t, J=7Hz), 4.0–4.3(4H, m),
5.09(1H, s), 6.12(1H, s),
7.41(1H, t, J=8Hz),
7.66(1H, dt, J=2Hz, 8Hz),
8.02(1H, dt, J=2Hz, 8Hz),
8.12(1H, t, J=2Hz)

2,6-Dimethyl-4-(3-nitrophenyl)-1,4-dihydropyridine-3,5-dicarboxylic acid 3-(3-benzoylthiopropyl) ester 5-[3-(2-cyanoethylthio)propyl]ester $^1$H-NMR(CDCl$_3$) δppm
1.90(2H, quintet, J=7Hz),
1.99(2H, quintet, J=7Hz), 2.38(3H, s),
2.40(3H, s), 2.52(2H, t, J=7Hz),
2.58(2H, t, J=6.5Hz), 2.72(2H, t, J=6.5Hz),
3.02(2H, t, J=7Hz), 4.0–4.3(4H, m),
5.12(1H, s), 5.85(1H, s),
7.41(1H, t, J=8Hz), 7.46(2H, t, J=8Hz),
7.58(1H, t, J=8Hz),
7.68(1H, dt, J=2Hz, 8Hz),
7.93(2H, d, J=8Hz),
8.02(1H, dt, J=2Hz, 8Hz), 8.14(1H, t, J=2Hz)

2,6-Dimethyl-4-(3-nitrophenyl)-1,4-dihydropyridine-3,5-dicarboxylic acid 3-methyl ester 5-[3(2-cyanoethylthio)propyl] ester $^1$H-NMR(CDCl$_3$) δppm
1.80(2H, m), 2.36(3H, s), 2.40(3H, s),
2.52(2H, t, J=7Hz), 2.61(2H, m),
2.74(2H, m), 3.68(3H, s), 4.15(2H, m),
5.09(1H, s), 5.88(1H, bs), 7.3–8.1(4H, m)

2,6-Dimethyl-4-(3-nitrophenyl)-1,4-dihydropyridine-3,5-dicarboxylic acid 3-ethyl ester 5-[3ester $^1$H-NMR(CDCl$_3$) δppm
1.25(3H, t, J=6Hz), 1.89(2H, m),
2.35(3H, s), 2.40(3H, s),
2.52(2H, t, J=6Hz), 2.62(2H, m),
2.74(2H, m), 4.14(2H, m),
4.15(2H, q, J=6Hz), 5.09(1H, s), 5.98(1H, bs), 7.3–8.2(4H, m)

2,6-Dimethyl-4-(3-nitrophenyl)-1,4-dihydropyridine-3,5-dicarboxylic acid 3-isopropyl ester -[3-(2-cyanoethylthio)propyl]ester $^1$H-NMR(CDCl$_3$) δppm
1.13(3H, d, J=6Hz), 1.27(3H, d, J=6Hz), 1.89(2H, m), 2.36(3H, s), 2.38(3H, s),
2.52(2H, t, J=6Hz), 2.62(2H, m),
2.75(2H, m), 4.15(2H, m), 4.97(1H, m),
5.08(1H, s), 5.93(1H, bs),
7.3–8.2(4H, m)

What is claimed is:

1. A 1,4-dihydropyridine derivative represented by the formula

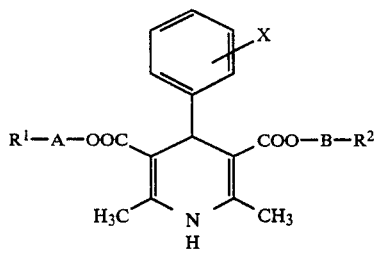

(I)

wherein $R^1$ is a hydrogen atom, an alkoxy group having 1 to 4 carbon atoms, a mercapto group, an alkylcarbonylthio group in which the alkyl group has 1 to 4 carbon atoms or a benzoylthio group, $R^2$ is a mercapto group, an alkylcarbonylthio group in which the alkyl group has 1 to 4 carbon atoms, a benzoylthio group or a 2-cyanoethylthio group, A and B are the same or different and are each an alkylene group having 1 to 4 carbon atoms, and X is a hydrogen atom, a halogen atom, a nitro group or a trifluoromethyl group.

2. 2,6-Dimethyl-4-(3-nitrophenyl)-1,4-dihydropyridine-3,5-dicarboxylic acid 3-ethyl ester 5-(2-acetylthioethyl) ester.

3. 2,6-Dimethyl-4-(3-nitrophenyl)-1,4-dihydropyridine-3,5-dicarboxylic acid 3-methoxyethyl ester 5-[3-(2-cyanoethylthio)propyl]ester.

4. 2,6-Dimethyl-4-(3-nitrophenyl)-1,4-dihydropyridine-3,5-dicarboxylic acid 3-methoxyethyl ester 5-(2-acetylthioethyl) ester.

5. 2,6-Dimethyl-4-(3-nitrophenyl)-1,4-dihydropyridine-3,5-dicarboxylic acid 3-methyl ester 5-(2-acetylthioethyl) ester.

6. 2,6-Dimethyl-4-(3-nitrophenyl)-1,4-dihydropyridine-3,5-dicarboxylic acid bis(3-acetylthiopropyl) ester.

* * * * *